United States Patent [19]

De Thomas et al.

[11] Patent Number: 5,149,836

[45] Date of Patent: Sep. 22, 1992

[54] PROCESS FOR THE PRODUCTION OF GAMMA BUTYROLACTONE THF IN PREDETERMINED AMOUNTS

[75] Inventors: Waldo De Thomas, Saylorsburg, Pa.; Paul D. Taylor, West Milford; Heinn F. Tomfohrde, III, Kinnelon, both of N.J.

[73] Assignee: ISP Investments Inc., Wilmington, Del.

[21] Appl. No.: 735,498

[22] Filed: Jul. 25, 1991

[51] Int. Cl.$^5$ ............................................. C07D 307/26
[52] U.S. Cl. ................................... 549/325; 549/326; 549/510
[58] Field of Search ................... 549/326, 325, 510

[56] References Cited

U.S. PATENT DOCUMENTS

| | | | |
|---|---|---|---|
| 3,065,243 | 11/1962 | Dunlop | 549/325 |
| 3,580,930 | 5/1971 | Miya et al. | 549/326 |
| 3,829,448 | 8/1974 | Kanetaka et al. | 549/325 |
| 3,853,922 | 12/1974 | Yamaguchi et al. | 549/325 |
| 3,894,054 | 7/1975 | Miya | 549/325 |
| 4,001,282 | 1/1977 | Miller | 549/325 |
| 4,006,165 | 2/1977 | Michalczyk et al. | 549/325 |
| 4,048,196 | 9/1977 | Broecker et al. | 549/325 |
| 4,772,729 | 9/1988 | Rao | 549/326 |
| 5,055,599 | 10/1991 | Budge | 549/325 |

FOREIGN PATENT DOCUMENTS 1901870 9/1969 Fed. Rep. of Germany.
2207914 2/1989 United Kingdom.

*Primary Examiner*—C. Warren Ivy
*Assistant Examiner*—Amelia A. Owens
*Attorney, Agent, or Firm*—Walter Katz; Marilyn J. Maue; Joshua J. Ward

[57] ABSTRACT

This invention provides a vapor phase process for the production of gamma-butyrolactone and tetrahydrofuran in a predetermined ratio by the steps of: hydrogenating a vapor mixture of maleic anhydride and excess hydrogen over a first bed of a Cu-Zn-Al catalyst, and directly contacting the crude reactor effluent therefrom with hydrogen over a second bed of Cu-Zn-Cr catalyst during a predetermined contact time and at a defined temperature, using selected amounts of catalyst in each bed.

4 Claims, No Drawings

PROCESS FOR THE PRODUCTION OF GAMMA BUTYROLACTONE THF IN PREDETERMINED AMOUNTS

BACKGROUND OF THE INVENTION

1. Field of the Invention

This invention relates to a process of vapor phase catalytic hydrogenation of maleic anhydride to gamma-butyrolactone (BLO) and tetrahydrofuran (THF), and, more particularly, to a multistage process in which the crude reactor effluent from the first stage hydrogenation is partially hydrogenated to tetrahydrofuran in a second stage hydrogenation to form a product mixture of gamma-butyrolactone and tetrahydrofuran in a selected ratio.

2. Description of the Prior Art

A continuous process is known for the manufacture of tetrahydrofuran by catalytic hydrogenation of maleic anhydride (MA) and/or succinic anhydride (SA) with the formation of gamma-butyrolactone (GBL) as an intermediate, in accordance with the following equations:

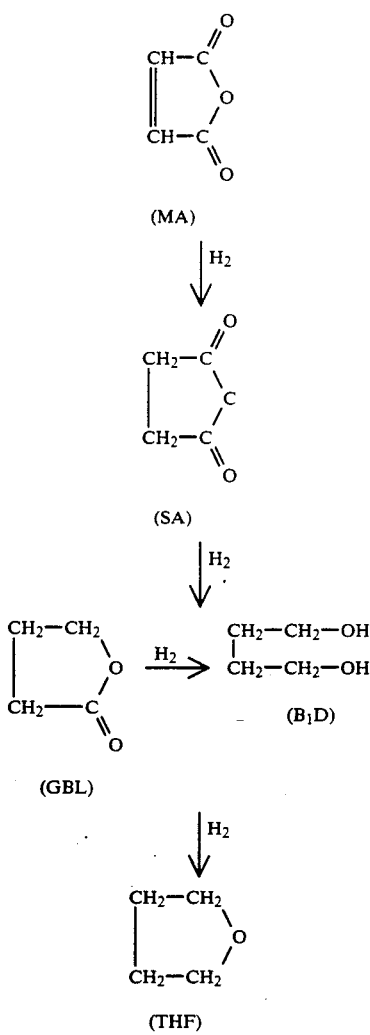

However, different mixtures, depending on the hydrogenation catalyst used, of intermediate products and end products, e.g. succinic acid, butyrolactone, tetrahydrofuran and butanediol, as well as propanol and butanol, and polymeric esters of the above compounds, are formed.

Various hydrogenation catalysts have been disclosed for carrying out such a hydrogenation process. See, for example, U.S. Pat. Nos. 3,065,243; 3,580,930; 3,829,448; 3,894,054; 3,853,922; 4,001,282; 4,105,674; 4,083,809; 4,006,165; 4,810,807; and EPA 332,140.

U.S. Pat. No. 4,048,196, for example, described a multistage process for the manufacture of butanediol and/or tetrahydrofuran from maleic anhydride or succinic anhydride via gamma-butyrolactone intermediate. In this process, (a) maleic anhydride or succinic anhydride was hydrogenated in the presence of gamma-butyrolactone over a fixed-bed catalyst containing nickel to give gamma-butyrolactone; then (b) the water formed during the hydrogenation was removed by feeding the reaction mixture to the middle section of a distillation column; then isolating water and gamma-butyrolactone, on one hand, and succinic anhydride and gamma-butyrolactone on the other; recycling the succinic anhydride and gamma-butyrolactone; and separating the gamma-butyrolactone and water by distillation; and (c) hydrogenating gamma-butyrolactone over a catalyst containing copper into butanediol and/or tetrahydrofuran. However, in this process, it was necessary to obtain the gamma-butyrolactone as the sole product of the hydrogenation of maleic anhydride, and, in a separate, off-line stage, to convert the isolated butyrolactone into butanediol and tetrahydrofuran.

Accordingly, it is an object of this invention to provide a process of vapor phase hydrogenation of maleic anhydride to a predetermined mixture of gamma-butyrolactone and tetrahydrofuran by multistage hydrogenation without separating any by-products or isolating the gamma-butyrolactone intermediate.

SUMMARY OF THE INVENTION

This invention provides a vapor phase process for the production of BLO and THF in a predetermined ratio in which a vapor mixture of maleic anhydride is hydrogenated in an excess of hydrogen with a first bed of a catalyst which produces BLO, such as a $Cu-Zn-Al_2O_3$ catalyst, followed directly by contacting the crude reactor effluent with hydrogen over a second bed of a catalyst which produces THF, such as a $Cu-Zn-Cr_2O_3$ catalyst, during a predetermined contact time and at a defined temperature, using selected amounts of catalyst in each bed.

DETAILED DESCRIPTION OF THE INVENTION

Definitions

"Activated Catalyst" is defined herein as a catalyst for hydrogenation of feed compound to butyrolactone having a defined catalyst composition and predetermined physical properties, which is prepared by reducing the catalyst composition, and then activating the reduced catalyst composition under prescribed activation conditions.

"Conversion" is defined herein as the percentage of feed compound consumed in the reaction.

"Selectivity" is defined herein as the percentages of butyrolactone and tetrahydrofuran produced as compared to the total amount of starting material consumed.

"Yield" of butyrolactone is defined as the product of conversion times selectivity.

"Feed Compound" is defined as maleic anhydride, succinic anhydride, maleic acid, succinic acid, or esters thereof, or mixture of the foregoing, which can be catalytically converted to butyrolactone by a vapor process.

"Other Product" is defined herein as including the compound tetrahydrofuran which is obtained in predetermined amounts herein.

"Contact Time" is defined herein as the time in seconds that the reactants are present in the catalyst zone, and is calculated by dividing the volume of the catalyst in the reactor by the volume of flow of the reactants per second under reactor conditions.

"Feed Rate" or "Space Velocity, LHSV", in hours$^{-1}$, is defined herein as the volume of liquid feed compound per hour per volume of catalyst used in the reactor.

"Feed Composition" is defined herein as the molar ratio of hydrogen to the feed compound in the vapor mixture.

"Percentages" are given by weight of the component in the composition.

FIRST STAGE HYDROGENATION

An activated catalyst for vapor phase catalytic hydrogenation of a feed compound selected from maleic anhydride, succinic anhydride, maleic acid, succinic acid, and mixtures thereof, to gamma-butyrolactone, in the first stage of the process of the invention, in a conversion of about 95% or more, and a selectivity of about 80% or more, is provided herein. The activated catalyst is capable of production of gamma-butyrolactone for at least 100 hours before reactivation of the catalyst, and for at least 2000 hours without requiring fresh catalyst, and is prepared by:

(a) providing a catalyst composition consisting essentially of about 30-65% by weight of CuO, preferably about 50-60%, about 18-50% by weight of ZnO, preferably about 20-25%, about 8-22% by weight of $Al_2O_3$, preferably about 15-20%, and about 0-5% by weight of a processing aid, preferably about 1-4% graphite, having a total pore volume of about 0.05 to 0.5 cc/g, preferably about 0.1 to 0.4 cc/g, and a surface area of about 20 to 120 m$^2$/g, preferably about 40 to 100 m$^2$/g, (b) reducing said catalyst composition with hydrogen in a gradually increasing hydrogen concentration of from about 0.5% to about 10% initial concentration of hydrogen in an inert diluent to 100% hydrogen in the final concentration under conditions of an increasing reduction temperature of about 150° to about 350° C. for about 5 to 20 hours, and (c) activating the reduced catalyst in hydrogen at an activation temperature of at least 400° C., preferably about 400° to 525° C., most preferably about 425° to 450° C., for a period of at least 8 hours, to provide an activated catalyst having a total pore volume of about 0.08 to 0.3 cc/g, preferably about 0.1 to 0.25 cc/g, and a surface area of about 15 to 100 m$^2$/g, preferably about 30 to 65 m$^2$/g.

The hydrogenation process during the first stage is carried out under predetermined, advantageous process conditions in which (1) a vapor mixture of the feed compound in hydrogen is provided at a molar ratio of hydrogen to feed compound of about 200:1 to 500:1; and (2) the vapor mixture is passed over the activated catalyst at (a) a pressure of about 50 to 500 psig, and (b) a feed rate space velocity of about 0.03 to 1.0 hours$^{-1}$, for (c) a contact time of less than about 10 seconds, at (d) a reaction temperature of about 200° to about 400° C.

A. PREPARATION OF ACTIVATED CATALYST FOR FIRST STAGE HYDROGENATION

1. Preparation of Suitable Catalyst Composition

The catalyst composition for the first stage hydrogenation consists essentially of Cu, Zn and Al, in the form of their oxides, in the amounts of about 30-65% by weight of CuO, preferably 50-60%, about 18-50% by weight of ZnO, preferably about 20-25%, and about 8-22% by weight $Al_2O_3$, preferably about 15-20%. The composition also may include, if desired, about 1-5% by weight of the composition of a processing aid such as graphite. A most preferred composition contains about 55% CuO, 23% ZnO, 18% $Al_2O_3$ and 4% graphite.

The catalyst composition may be prepared conveniently by decomposing the corresponding carbonates or nitrates to the oxides at an elevated temperature, generally about 250° to 450° C. The metal carbonates, in turn, can be obtained easily by precipitation of the carbonate compounds from an aqueous reaction mixture of the metal nitrates and a suitable quantity of an alkali metal carbonate. Upon filtering, drying and calcining the carbonates, the oxides are provided in the desired amounts of the composition.

In addition to the compositional requirements for this catalyst, it is desirable that the catalyst composition possess certain physical properties which enhances its performance in the process. Accordingly, it is preferred that the catalyst composition possess a total pore volume of about 0.05 to 0.5 cc/g, preferably about 0.1 to 0.4 cc/g, and a surface area of about 20 to 120 m$^2$/g, preferably about 40 to 100 m$^2$/g.

2. Reduction of Catalyst Composition

In this step, the catalyst composition is reduced by the conventional method of heating hydrogen at low temperatures to provide a reduced form of the composition. Accordingly, this step is carried out suitably at a reduction temperature of about 170°-300° C., under an inert atmosphere, e.g. that of nitrogen, to which hydrogen is slowly added at a rate such as to avoid a build-up of temperatures above 300° C. within the catalyst bed. The gas flowing over the catalyst bed then is gradually enriched with hydrogen as the temperature is slowly raised.

3. Activation of Reduced Catalyst

In accordance with the present invention, the reduced catalyst is subjected to an activation step which enables the activated catalyst to provide desired high conversion and high selectivity during prolonged use in the process without requiring excessive reactivations or substitution of fresh, activated catalyst. The activation step is accomplished by heating the reduced catalyst in hydrogen at a temperature of at least 400° C., preferably at about 400°-525° C., and most preferably, at 425°-450° C. The activation heat treatment effects at least a change in the physical properties of the catalyst which favorably impacts upon conversion, selectivity, and durability of the thus-activated catalyst during production of gamma-butyrolactone over a period of several thousand hours of continuous operation of the process. In particular, it is observed that activation effects a reduction of the total pore volume of the activated catalyst to about 0.08 to 0.3 cc/g, preferably about 0.1 to 0.25 cc/g, and the surface area to about 25 to 100 m$^2$/g, preferably about 30 to 65 m$^2$/g.

B. FORMATION OF VAPOR MIXTURE OF FEED COMPOUND IN HYDROGEN

1. Method of Formation

Vaporization of maleic anhydride into hydrogen to form the vapor mixture may be carried out in the manner described in the reference patents. However, it is preferred that the vapor mixture of the feed compound in hydrogen is obtained by forming finely divided droplets of the feed compound in a reactor by passing the compound through a spray nozzle and vaporizing the droplets rapidly with hot, recycle hydrogen gas introduced into the reactor and directed at the droplets. Accordingly, a source of the feed compound, such as molten maleic anhydride at about 80° C., is pumped at a suitable pressure and flow rate into a vaporizer vessel through a spray nozzle which converts the mass of molten liquid into fine droplets within the interior of the vessel. A hot, recycle hydrogen gas stream then is introduced into the vessel at a temperature of about 160° to 300° C. The hot, recycle hydrogen gas immediately vaporizes the droplets, that is, before they can reach the walls of the vessel where they could coalesce into a liquid stream, and before they can polymerize and cause fouling of the vaporization process.

2. Molar Ratio of Hydrogen to Feed Compound in Vapor Mixture

This ratio suitably is maintained in the range of about 200:1 to 500:1, and, preferably 230:1 to 280:1. Within this vapor ratio, the process can provide a conversion of 100% and a selectivity of from 85% to 95%. Lower H$_2$/feed compound vapor mixture ratios, e.g. 100:1, on the other hand, result in severe deterioration of selectivity, e.g. to 82% or lower. These lower selectivity ratios also are consistent with an observed catalyst deactivation after less than 100 hours of operation.

C. OTHER PROCESS PARAMETERS

1. Contact Time

The contact time of the reactants with the activated catalyst of the invention suitably is less than about 10 seconds, preferably about 2.0 to 3.5 seconds, and, most preferably, about 2.5-3.0 seconds. In this contain time range, the process will provide a conversion of about 100% and a selectivity of 85-95%. Shorter contact times than the suitable range will favor increased selectivity, however, at the expense of substantially decreased conversion, to below 80%.

2. Pressure during Hydrogenation Reaction

The catalytic hydrogenation process of the invention is carried out at low pressures, suitably in the range of about 50 to 500 psig, and, preferably, about 75 to 250 psig.

3. Feed Rate, or Space Velocity, LHSV (in hours$^{-1}$)

The feed rate of the liquid feed compound over a given amount of catalyst in the process suitably is about 0.03 to 1.0 hours$^{-1}$, preferably, about 0.05 to 0.25 hours$^{-1}$, and, most preferably, about 0.07-0.15 hours$^{-1}$.

D. RESULTS

1. Conversion Percentages

The conversion of feed compound consumed during the reaction is substantially 100%.

2. Selectivity to Butyrolactone

The first stage in the process of the invention produces several compounds, predominately butyrolactone. Other compounds such as tetrahydrofuran, butanol and propanol, also are produced, however, only in small amounts. In the present process, selectivity with respect to the production of butyrolactone is greater than 80%, and usually about 90-95%.

3. Lifetime of Catalyst

The activated catalyst of the invention can achieve the results described herein over a production period of 2000 hours or more. Usually the activated catalyst is reactivated after the first 100 hours, and then again after about 500 hours. Reactivation is carried out by heating the catalyst in situ in hydrogen at the activation temperature, preferably at about 425°-450° C. for 8-12 hours.

The activated catalyst of the invention may be used in a number of different forms, sizes and shapes, the choice of which is dependent upon whether or not the process of the present invention is carried out in a fixed bed reactor, or with a fluidized bed reactor, since the catalyst can be adapted to suit either of these purposes. Accordingly, the catalyst may be present in the process as a pellet, ring, sphere, extrudate, etc.

The first stage of the invention will now be illustrated by the following non-limiting examples.

EXAMPLE 1

A. Preparation of Activated Catalyst For First Stage Hydrogenation

1. Preparation of Catalyst Composition

A solution of 372 g of copper nitrate, 170 g of zinc nitrate and 125 g of aluminum nitrate in 1 liter of water was prepared at 50° C. Then a solution prepared from 350 g of sodium carbonate in 1 liter of water at 50° C. was slowly added to the metal nitrate solutions to precipitate the respective catalyst precursors as carbonates. The resultant slurries then were filtered and washed in small portions with 2 liters of water at 50° C. After drying at 120° C. for 2 hours, and calcining at 250° C. for six hours, 200 g of catalyst composition was obtained. Then 3% by weight of graphite was admixed with the calcined product. The resultant composition analyzed 55% CuO, 23% ZnO, 18% Al$_2$O$_3$ and 4% graphite. The total pore volume was 0 1–0.4 cc/g, and the surface area was 20 to 120 m$^2$/g. The resulting calcined catalyst powders were tableted to ⅛ inch diameter pellets.

2. Reduction of Catalyst Composition

The catalyst composition prepared above was reduced by hydrogen in a generally inert atmosphere by slowly adding hydrogen to nitrogen and increasing the reduction temperature from 170° C. to 300° C., according to the sequence shown in Table 1 below. The catalyst then were held at the final temperature until no further formation of any water of reduction was observed, whereupon the reduced catalyst was ready for activation.

TABLE 1

Reduction of Catalyst Composition with Hydrogen at 170°-300° C.

| Temp (°C.) | Press. (psig) | $N_2$ (cc/min) | $H_2$ (cc/min) | $H_2$ (%) | Time (hrs) |
|---|---|---|---|---|---|
| 170 | 150 | 1000 | 10 | 1 | 0.5 |
| 170 | 150 | 1000 | 20 | 2 | 12 |
| 200 | 150 | 1000 | 40 | 4 | 2 |
| 250 | 150 | 1000 | 80 | 8 | 2 |
| 300 | 150 | 1000 | 160 | 16 | 2 |

3. Activation of Reduced Catalyst

The reduced catalyst then was activated at 425° C. in hydrogen for 12 hours as shown in Table 2 below.

TABLE 2

| Temp (°C.) | Press. (psig) | $N_2$ (cc/min) | $H_2$ (cc/min) | $H_2$ (%) | Time (hrs) |
|---|---|---|---|---|---|
| 425 | 150 | 0 | 1000 | 100 | 12 |

The activated catalyst had a total pore volume of about 0.1 to 0.25 cc/g, and a surface area of about 30 to 65 m²/g, and was ready for use in the process for producing gamma-butyrolactone.

B. FIRST STAGE VAPOR PHASE CATALYTIC HYDROGENATION

A stainless steel, fixed bed reactor tube having an internal diameter of 1.5 inches and a length of 12 inches was packed with 400 g. of the activated catalyst prepared above. A feed mixture of maleic anhydride in hydrogen at a mole ratio of hydrogen to maleic anhydride of 230:1, and at a space velocity, LHSV, of 0.1 hours$^{-1}$, was obtained by feeding molten maleic anhydride into a hydrogen stream. The vapor mixture was introduced into the reactor at a pressure of 150 psig and an inlet temperature of 245° C. After a catalyst contact time of 2.6 seconds, the products exited the catalyst bed at an outlet temperature of 275° C. The process was run continuously for 100 hours. Conversion was 100% and selectivity was 88% to butyrolactone. Then the catalyst was reactivated in situ at 425° C. in 100% hydrogen for 12 hours and production was continued for an additional 400 hours. Conversion was 100% and selectivity increased to 95%.

EXAMPLE 2

The procedure of Example 1 was followed using the sequence of reduction and activation shown in Table 3 below on the catalyst composition.

TABLE 3

| Temp (°C.) | Press. (psig) | $N_2$ (cc/min) | $H_2$ (cc/min) | $H_2$ (%) | Time (hrs) |
|---|---|---|---|---|---|
| Reduction | | | | | |
| 170 | 75 | 1000 | 10 | 1 | 0.5 |
| 170 | 75 | 1000 | 20 | 2 | 12 |
| 200 | 75 | 1000 | 40 | 4 | 2 |
| 250 | 75 | 1000 | 80 | 8 | 2 |
| 300 | 150 | 1000 | 160 | 16 | 2 |
| Activation | | | | | |
| 425 | 150 | 0 | 1000 | 100 | 12 |

The resulting activated catalyst was used in the hydrogenation process at an inlet temperature of 246° C. and an outlet temperature of 250° C. The space velocity, LHSV, was 0.08. Conversion during the run was 100% and selectivity was 92%.

EXAMPLE 3

Examples 1 and 2 were repeated using activation temperatures of 400° and 475° C. The thus-activated catalyst gave similar results in the hydrogenation process with respect to conversion and selectivity.

EXAMPLE 4

The procedure of Examples 1-3 were repeated using a catalyst composition of 34-37% CuO, 37-47% ZnO, 9-12% $Al_2O_3$ and 4% graphite. The activated catalyst provided a conversion of 100% and a selectivity of 85% after 100 hours.

SECOND STAGE HYDROGENATION

The crude reactor effluent containing predominately BLO from the first stage hydrogenation then is passed directly over a second stage hydrogenation catalyst having the following composition:

TABLE 4

SUITABLE COMPOSITION OF SECOND STAGE CATALYST

| | Suitable (wt. %) | Preferred (wt. %) |
|---|---|---|
| CuO | 10-50% | 20-25% |
| ZnO | 30-65% | 50-60% |
| $Cr_2O_3$ | 3-20% | 8-15% |

The composition also may include about 1-5% of graphite as a processing aid.

Preferably, the second stage catalyst is activated according to the procedure described for the first stage catalyst, and most preferably, at the same time in the same reactor.

The residence time of the crude reactor effluent feed in the second bed catalyst suitably is about 1-4 seconds, preferably about 1.5-2 seconds; and the reaction temperature of the second bed is about 200°-350° C., preferably about 250°-280° C.

PROCESS CONDITIONS WHICH AFFECT THE BLO-THF RATIO IN THE PRODUCT MIXTURE

The data in Table 5 below shows that the volume ratio of the catalyst in the first bed to that of the catalyst in the second bed will significantly affect the BLO/THF ratio of the product. Table 5 also shows that the relative amounts of BLO and THF produced after the second stage hydrogenation also can be controlled by the temperature of the second catalyst bed. For example, a second bed temperature of about 250° C. will provide higher amounts of BLO, while a temperature of 280° C. will increase the amount of THF produced.

TABLE 5

| Volume Ratio of Cat. in Bed #1 Cat. in Bed #2 | Second Bed Temp. (°C.) | Contact Time (sec.) | Selectivity (%) BLO | Selectivity (%) THF |
|---|---|---|---|---|
| 1.0 | 250 | 1.5 | 35 | 63 |
| 1.0 | 280 | 2.0 | 15 | 83 |
| 2.5 | 250 | 1.5 | 83 | 15 |
| 2.5 | 280 | 2.0 | 53 | 45 |
| 4.0 | 250 | 1.5 | 92 | 7 |
| 4.0 | 280 | 2.0 | 68 | 30 |

The crude reactor effluent from the second stage hydrogenation then is condensed and fractional distilled to provide predetermined amounts of BLO and THF in isolated and separate form. The overall conversion of the process to BLO and THF is about 90-100%.

While the invention has been described with particular reference to certain embodiments thereof, it will be understood that changes and modifications may be made which are within the skill of the art. Accordingly, it is intended to be bound only by the following claims, in which:

What is claimed is:

1. A multistage vapor phase process for the production of gamma-butyrolactone and tetrahydrofuran in a predetermined selectivity ratio of about 15-92% to 7-83%, respectively, at an overall conversion of 90-100%, which comprises: in a first stage, hydrogenating a feed mixture of maleic anhydride and excess hydrogen over a first bed of a catalyst of about 30-65wt. % CuO, 18-50 wt. % ZnO and 8-22% $Al_2O_3$, to produce a crude reactor effluent containing predominately gamma-butyrolactone, and, in a second stage, directly contacting said crude reactor effluent with hydrogen over a second bed of a catalyst of about 10-50 wt. % CuO, 30-65 wt. % ZnO and 3-20 wt. % $Cr_2O_3$, which can convert said gamma-butyrolactone into tetrahydrofuran, during a predetermined contact time of about 1-4 seconds, and at a predetermined temperature of about 200°-350° C., the relative amount of gamma-butyrolactone and tetrahydrofuran obtained in said second stage being predetermined by the defined contact time over the second bed, and the selected volume ratio of about 1:1 to 1:4 of the respective first and second catalysts in said beds, at said second bed temperature.

2. A multistage process according to claim 1 wherein said second catalyst bed is operated for a contact time of about 1.5-2. seconds and at a temperature of about 200°-280° C.

3. A multistage process according to claim 1 wherein said second stage catalyst comprises about 20-25 wt. % CuO, 50-60 wt. % ZnO and 8-15% wt. % $Cr_2O_3$.

4. A multistage process according to claim 1 wherein the first bed catalyst is activated by reducing in hydrogen and then heating in hydrogen at a temperature of at least 400° C.

* * * * *